(12) United States Patent
McCain et al.

(10) Patent No.: US 11,749,091 B2
(45) Date of Patent: Sep. 5, 2023

(54) ELECTRONIC MATERIAL SLEEVE FOR MEDICAL DEVICES

(71) Applicants: Aisha McCain, Pittsburg, CA (US); Annemarie Sheets, Pittsburg, CA (US)

(72) Inventors: Aisha McCain, Pittsburg, CA (US); Annemarie Sheets, Pittsburg, CA (US)

(73) Assignee: Create To Overcome LLC, Pittsburg, CA (US)

( * ) Notice: Subject to any disclaimer, the term of this patent is extended or adjusted under 35 U.S.C. 154(b) by 0 days.

(21) Appl. No.: 17/736,556

(22) Filed: May 4, 2022

(65) Prior Publication Data

US 2023/0011993 A1 Jan. 12, 2023

Related U.S. Application Data

(60) Provisional application No. 63/221,213, filed on Jul. 13, 2021, provisional application No. 63/220,186, filed on Jul. 9, 2021.

(51) Int. Cl.
*G08B 21/24* (2006.01)
*G08B 7/06* (2006.01)

(52) U.S. Cl.
CPC ............... *G08B 21/24* (2013.01); *G08B 7/06* (2013.01)

(58) Field of Classification Search
CPC .................................. G08B 21/24; G08B 7/06
See application file for complete search history.

(56) References Cited

U.S. PATENT DOCUMENTS

| | | | | |
|---|---|---|---|---|
| 10,204,213 B2* | 2/2019 | Doswell | ............... | A61B 5/1112 |
| 2011/0226242 A1* | 9/2011 | Von Hollen | ...... | A61M 15/0023 |
| | | | | 128/203.12 |
| 2014/0000598 A1* | 1/2014 | Sutherland | ........ | A61M 15/0065 |
| | | | | 128/203.12 |
| 2016/0144141 A1* | 5/2016 | Biswas | .................. | G16H 20/40 |
| | | | | 128/200.23 |
| 2016/0325057 A1* | 11/2016 | Morrison | ............... | G16H 40/63 |
| 2017/0325734 A1* | 11/2017 | Sutherland | ........ | A61M 15/0041 |
| 2019/0021400 A1* | 1/2019 | Fornarelli | ............... | A24F 40/51 |

* cited by examiner

*Primary Examiner* — Kam Wan Ma
(74) *Attorney, Agent, or Firm* — Cynthia S. Lamon; Lamon Patent Services (57) ABSTRACT

An electronic material sleeve has a length and wall thickness and is adapted to fit over a hand-held emergency medication dispensing device via material elasticity, the sleeve including at least a microprocessor and associated circuitry encapsulated within a wall of the electronic sleeve, the microprocessor adapted to support at least one computer aided task and at least one wireless communications technology, the sleeve having at least one encapsulated batter, a partly encapsulated charge port for charging the at least one battery, at least one LED partially encapsulated within a wall of the electronic sleeve, at least one audio speaker partially encapsulated within a wall of the electronic sleeve, and at least one eccentric rotating motor (ERM) adapted to vibrate encapsulated within a wall of the electronic sleeve, the sleeve capable of performing one or more tasks in response to a command signal.

18 Claims, 8 Drawing Sheets

*Fig. 1*

*Prior Art*

ELECTRONIC MATERIAL SLEEVE FOR MEDICAL DEVICES

CROSS-REFERENCE TO RELATED DOCUMENTS

The present invention claims priority to a U.S. provisional patent application Ser. No. 63/221,213 entitled ELECTRONIC AUTO-INJECTOR SLEEVE DEVICE filed on Jul. 13, 2021, and to a U.S. provisional patent application Ser. No. 63/220,186 entitled ELECTRONIC INHALER SLEEVE DEVICE, filed on Jul. 9, 2021 disclosure of which is included herein at least by reference.

BACKGROUND OF THE INVENTION

1. Field of the Invention

The present invention is in the field of medical devices and pertains particularly to methods and apparatus for medically purposed aftermarket devices and pertains particularly to a material covering enhanced by electronics for encasing or otherwise encapsulating an emergency medication dispensing device.

2. Discussion of the State of the Art

Medications for breathing problems, such as asthma and chronic obstructive pulmonary disease (COPD), are commonly delivered directly to the lungs. These medications include albuterol and steroids, among others. A meter dose inhaler (MDI) is commonly termed an inhaler in the art. Most of the inhaler devices are MDIs. For example, the drug albuterol delivered by MDI is the fastest way to reverse an asthma attack. The medicine allows the muscles around branches of the lungs to relax. Asthma is a common, chronic respiratory disease that affects approximately 26 million people in the US. It is the most common chronic disease in childhood, affecting an estimated 7 million children. The estimate of lost work and school time from asthma is approximately 100 million days of restricted activity. Approximately 500,000 annual hospitalizations (40.6% in individuals aged 18 years or younger) are due to asthma. Each year, an estimated 1.7 million people (47.8% of them aged 18 years or younger) require treatment in an emergency department. For 2010, the annual expenditures for health and lost productivity due to asthma was projected to be $20.7 billion.

Patients with poorly controlled asthma develop long-term changes over time (i.e., with airway remodeling). This can lead to chronic symptoms and a significant irreversible component to their disease. Mortality in the US is approximately 1 per 100,000, and death often occurs in young people due to treatment and management failure. People who live with asthma must keep their inhaler with them in body of an attack, however, it is easy for a person to forget or lose the inhaler. Asthma can quickly become so severe that speaking or calling for help is impossible. Seconds can make the difference between life and death. While many medical devices including MDIs have been fabricated with electronic capabilities including enabling a mobile application to track device usage, the capabilities are brand specific and add to the costs of the device itself limiting availability to certain manufactured devices.

Medications for severe allergic reactions in people, such as those due to insect bites, insect stings, certain foods, drugs, or other substances are commonly delivered directly to the muscle (intramuscular) or to the skin (subcutaneous). The delivered medication is typically Epinephrine. Epinephrine may be delivered through a needle that is part of an auto-injector device, an example of which is an Auto-Injector™ device, a popular brand of such auto-injector devices. Epinephrine acts very swiftly once delivered and improves breathing, stimulates the heart muscle, raises a dropping blood pressure reading, reverses hives, and reduces swelling of the face, lips, and throat. Severe allergies affect approximately 50 million people in the US. Allergic reactions occur in approximately 40% of children. Allergic reactions are the sixth leading cause of chronic illness in the United States. The estimate of lost work and school time from allergic reactions is approximately 32 hours per week per sufferer during peak allergy seasons. Severe allergic reactions to foods result in approximately 30,000 emergency room visits per year in the United States.

The annual cost of treating allergic reactions exceeds 18 billion dollars. About 32 million people have food allergies with shellfish leading, followed by peanuts and then tree nuts. In children milk is in the top spot for an allergic food followed by eggs and then peanuts. Penicillin takes the top spot for those with drug allergies. People who live with sever allergies must keep their auto-injector device (Body) with them constantly in body of an attack, however, it is easy for a person to forget or lose an Body™ or any other brand of auto-injector device. An allergic reaction can quickly become so severe that speaking or calling for help is impossible. Seconds can make the difference between life and death. People may misplace or lose their epi pens and are at risk until they procure a replacement device.

Therefore, what is clearly needed is an electronically enhanced elastic material sleeve that may be custom fit to at least one form of a dedicated aftermarket emergency medication dispensing device carried by a user for medical maintenance and or medical emergency applications.

BRIEF SUMMARY OF THE INVENTION

According to an embodiment of the present invention, an electronic material sleeve is provided and adapted to fit over a hand-held emergency medication dispensing device. The electronic material sleeve is elastic having a length and a wall thickness, a microprocessor and associated circuitry encapsulated within a wall of the electronic material sleeve, the microprocessor adapted to support at least one computer aided task, at least one wireless communications technology, at least one battery encapsulated within a wall of the electronic material sleeve providing power to the microprocessor and other electronic components, a charge port accepting a charge cable adapted for charging the at least one battery, at least one LED partially encapsulated within a wall of the electronic material sleeve, at least one audio speaker partially encapsulated within a wall of the electronic material sleeve, and at least one eccentric rotating motor (ERM) adapted to vibrate encapsulated within a wall of the electronic material sleeve. The electronic material sleeve performs one or more tasks in response to a command signal.

In one embodiment, the emergency medication dispensing device is a metered dose inhaler (MDI). In another embodiment, the emergency medication dispensing device is an epinephrine auto-injector device. In a variation of this embodiment, the auto-injector device is an epinephrine auto-injector (Epi Pen™). In one embodiment, the electronic material sleeve further includes a transparent window enabling visual access to instructions printed on the emergency medication dispensing device. In one embodiment, the at least one LED may flash for visual reference, the at least one speaker may emit sound for audio reference, and the electronic motor may vibrate for tactile reference upon receipt of a wireless command from another electronic device.

In another embodiment, the at least one LED may flash for visual reference, and the at least one speaker may emit sound for audio reference, and the electronic motor may vibrate for tactile reference upon detection of breech of an amount of distance established as a maximum boundary between the electronic material sleeve and another electronic device having a wireless connection to the electronic material sleeve. In a variation of this embodiment, the breech of distance is detected locally on the material electronic sleeve. In one embodiment, the command signal is received from a mini electronic accessory device or fob device using radio frequency identification (RFID) wireless technology. In another embodiment, the command signal is received from a mobile computing appliance or the fob device using wireless local area network signaling or a version of Bluetooth™ wireless technology. In a variation of this embodiment, the mobile computing appliance is a cellular phone.

In one embodiment, the electronic material sleeve, further includes a network modem and global positioning satellite (GPS) module. In this embodiment, the electronic material sleeve further includes an emergency contact button partially encapsulated within a wall of the electronic material sleeve. In this embodiment, one of one or more tasks performed is a task of connecting to a network access point and an emergency responder dispatch service as a result of an activation of the emergency contact button and sending a request for service with GPS location coordinates.

In one embodiment, the material wall thickness is larger on one side of the sleeve wherein the larger thickness area is host to the encapsulated and partially encapsulated electronics. In one embodiment, the electronic material sleeve further includes a memory device encapsulated within a wall of the electronic material sleeve, the memory device containing data about the patient including medical information, emergency service contact information, and contact information of family and friends. In another embodiment, the electronic material sleeve further includes a secure digital (SD) memory card, the memory card containing data about the patient including medical information, emergency service contact information, and contact information of family and friends. In one embodiment, the charge port also functions as a data port for transfer of data to or from the electronic material sleeve. In one embodiment, one of the one or more tasks performed is recording medication use events to determine reportable statistics including usage frequency, dose amount, and medication amount remaining in a loaded cartridge.

DETAILED DESCRIPTION OF THE INVENTION

In various embodiments described in enabling detail herein, the inventor provides a unique electronic material sleeve fitted to an emergency medication dispensing device, the sleeve adapted to be tracked and communicated with via digital wireless communication. A goal of the present invention is to enable a user to locate his or her emergency medication dispensing device using a mini tracking fob device or using a mobile computing appliance that may or may not host an executable tracking application. Another goal of the invention is to enable automatic and manual emergency alert reporting from the electronic material sleeve to a third-party emergency responder service that may dispatch a medical response person or personnel locally. A further goal of the invention is to enable data collection from memory provided in the sleeve electronics for subsequent utilization in locating the electronic sleeve, monitoring the charge state of the electronic sleeve, or in monitoring a patient's medical dispense frequency and pattern including current canister volume. The present invention is described using the following examples, which may describe more than one relevant embodiment falling within the scope of the invention.

Figure 1:
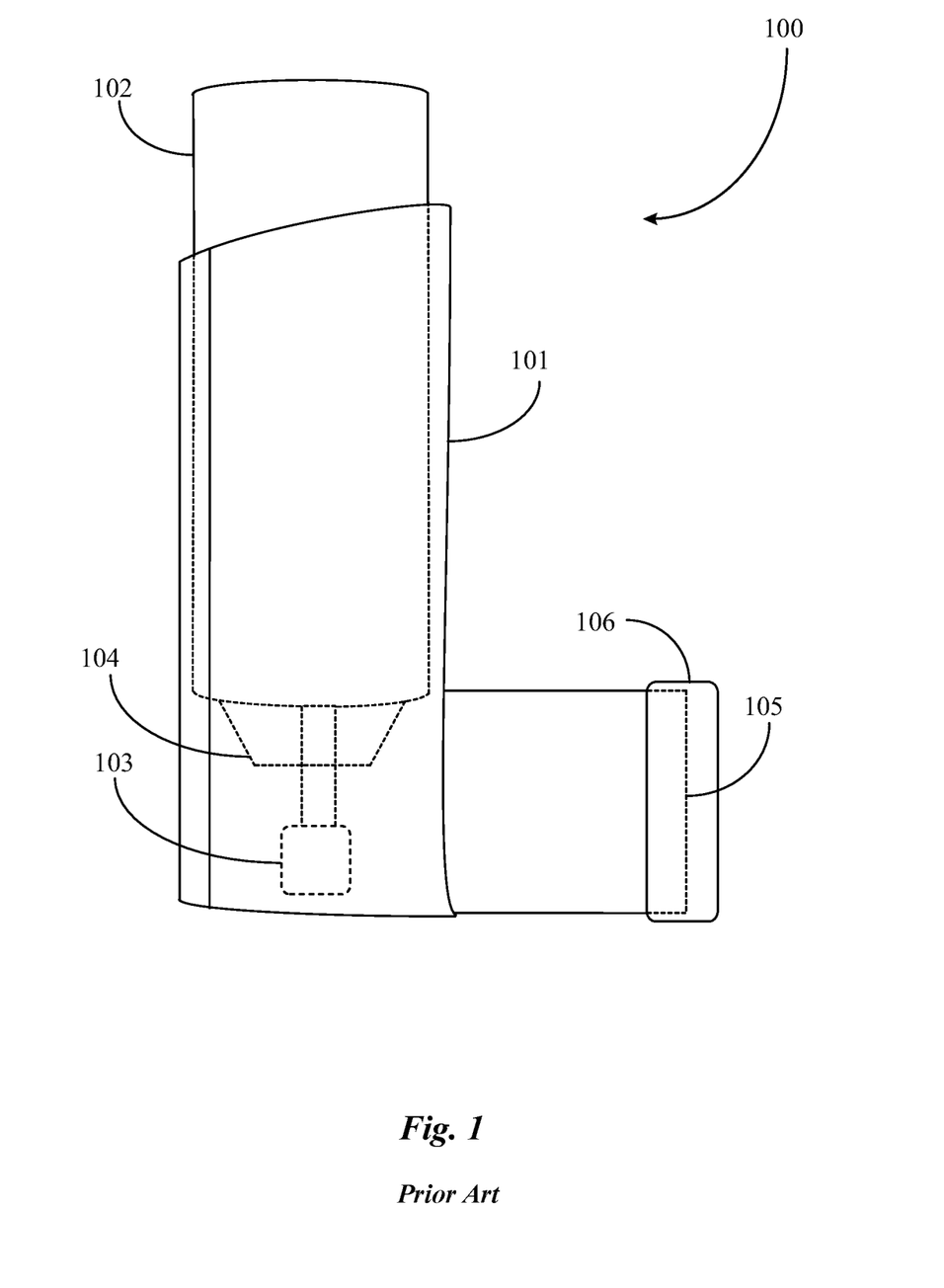
FIG. 1 is a side elevation view of an MDI according to current art.

FIG. 1 is a side elevation view of an emergency medication dispensing device, in this embodiment a metered dose inhaler (MDI) 100 according to current art. MDI 100 is a well-known stock medical device that is adapted to deliver metered doses of one of a variety of aerosol medications such as albuterol medication, for example from a pressurized cartridge containing the medication. MDI 100 depicts basic essential components of an inhaler device of a basic design. MDI 100, also referred to herein as an inhaler device or an inhaler has a generally rigid plastic body 101 that may be a molded rigid plastic or composite body. Body 101 may include a tubular section, which may be a contiguous part of body 101 that may typically be oriented substantially vertically when held for use by a patient inhaling a dose of medication from the device. Body 101 of MDI 100 may include a tubular mouthpiece extension disposed angularly from the vertical tubular section of body 101.

Body 101 may be a molded contiguous form or two body sections that may be assembled in a sealable manner to form a working body 101. It is noted herein that the design of body 101 may be of a different geometric shape than with an annular or tubular design as is the body sections comprising body 101. MDI inhaler 100 includes an aerosol medication canister 102 adapted to contain the medication under pressure. Medication canister 102 is adapted to fit into the substantially vertical section of body 101 in the manner of loading a pressurized medical cartridge for subsequent use. MDI 100 includes an actuator 103 to actuate release of the pressurized medication in a measured amount as an aerosol that a user breathes in through a mouthpiece referenced herein as mouthpiece 105. The actuator 103 is connected to canister 102 by a pressure release stem 104. A cap 106 may be provided to cover mouthpiece 105.

In use of MDI 100, a patient may position the medical device against the lips and operate actuator 103 causing a release of medicine from canister 102 in the form of an aerosol disposed to the inhalant end of body 101 and inhaled by the patient through mouthpiece 105. In typical use, actuator 103 is connected by pressure release stem 104 to the center of the dispensing end of medication canister 102 and is operable by a patient to cause a metered dose of medicine to be dispensed from canister 102 into the lower tubular portion of body 101 for the patient to inhale. It is noted herein that there are numerous designs available for MDIs including those having different angular arrangements between the substantially vertical tube holding the medication canister and the tubular mouthpiece section.

Figure 2:
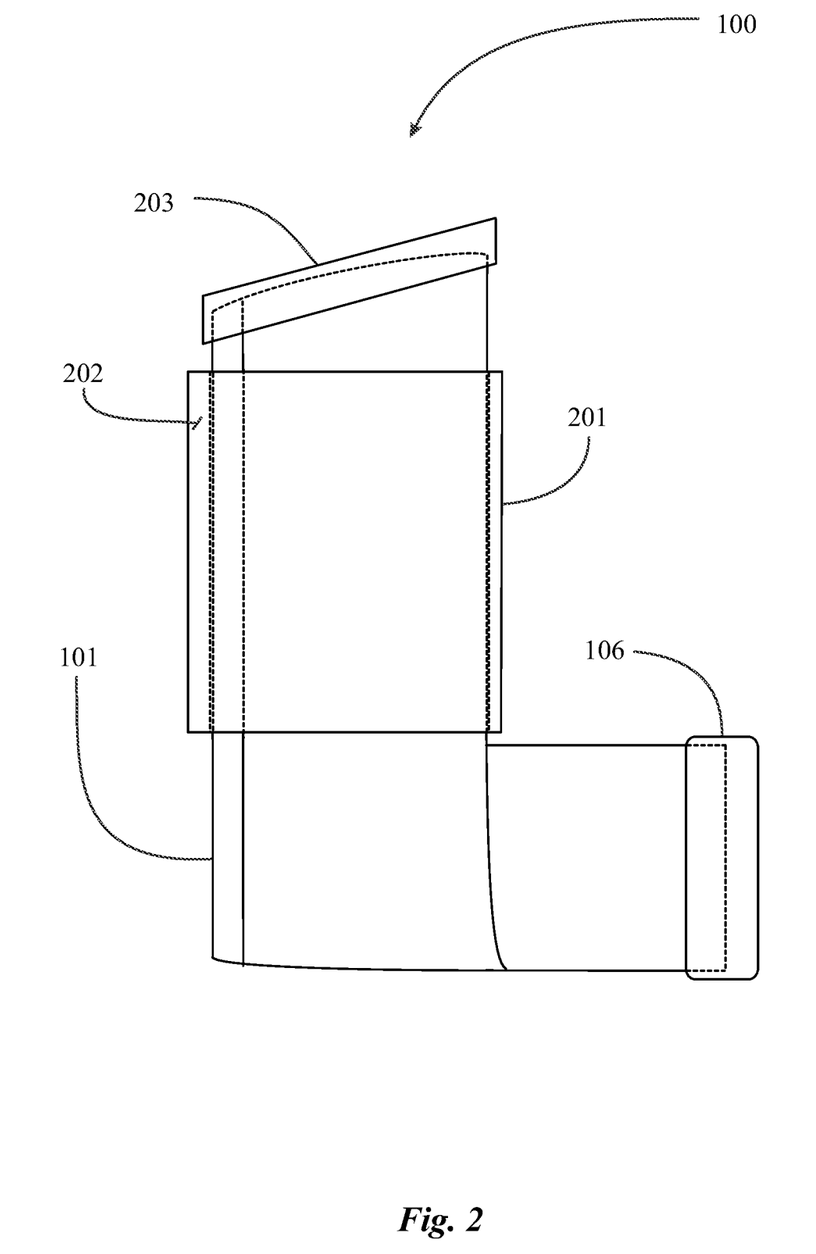
FIG. 2 is a side view of the MDI of FIG. 1 with an electronic material sleeve according to an embodiment of the present invention.

FIG. 2 is a side view of MDI 100 of FIG. 1 adapted with an electronic material sleeve 201 according to an embodiment of the present invention. In this embodiment, MDI 100 is modified with the application of an electronic material sleeve 201 that is adapted to be custom fitted over rigid plastic body 101. In this view, MDI 100 includes a top cap 203 that is not depicted in FIG. 1. Medication canister 102 is not depicted in this view for the purpose of clarity.

Electronic sleeve 201 may be molded in a tubular form from a medical grade elastic material like a silicone rubber or a suitable composite having elasticity. Electronic sleeve 201 has an inside diameter that is uniform in this body and that is smaller than the stock outside diameter of rigid plastic body 101. In a preferred embodiment, the material comprising electronic sleeve 201 is latex free, BPA free, water resistant, and of a medical grade material that can be sterilized. Electronic sleeve 201 may be stretched over and fitted onto the vertical tubular section of rigid plastic body 101 in a manner that is secure due to the elastic tension inherent to the sleeve material. Other than silicone rubber, similar elastic materials like neoprene rubber, or composites thereof may be substituted therefor without departing from the spirit and scope of the present invention.

Electronic sleeve 201 has a wall thickness and an outside diameter wherein the wall thickness is sufficient to enable encapsulation of mini electronic components and circuitry during fabrication of the sleeve. In one embodiment electronic sleeve 100 has a uniform wall thickness. No electronics components or circuitry is depicted in the embodiment but may be presumed present and encapsulated within the wall of electronic sleeve 201. In this view, an electronics footprint 202 is depicted defining a preferred general location for disposition of the electronics components of sleeve 201.

Footprint 202 may be positioned on the side of MDI 100 away from mouthpiece 105 (FIG. 1) covered in this view by cap 106, which may be a rubber or polymer cap. In one embodiment, electronic sleeve 201 has a thicker wall at the side of electronics footprint 202, however this is not required to practice the present invention. In one embodiment, electronics footprint 202 may be orientated in other directions relative to the given orientation of MDI 100 without departing from the spirit and scope of the present invention. Electronics footprint 202 functions according to design functionality dependent upon the electronics capabilities of the components encapsulated within the sleeve material of electronic sleeve 201. A patient may remove cap 203 to install electronic sleeve 201 over body 101 in a manner as to position the sleeve securely over body 101 down toward the lower tube section of body 101.

Figure 3:
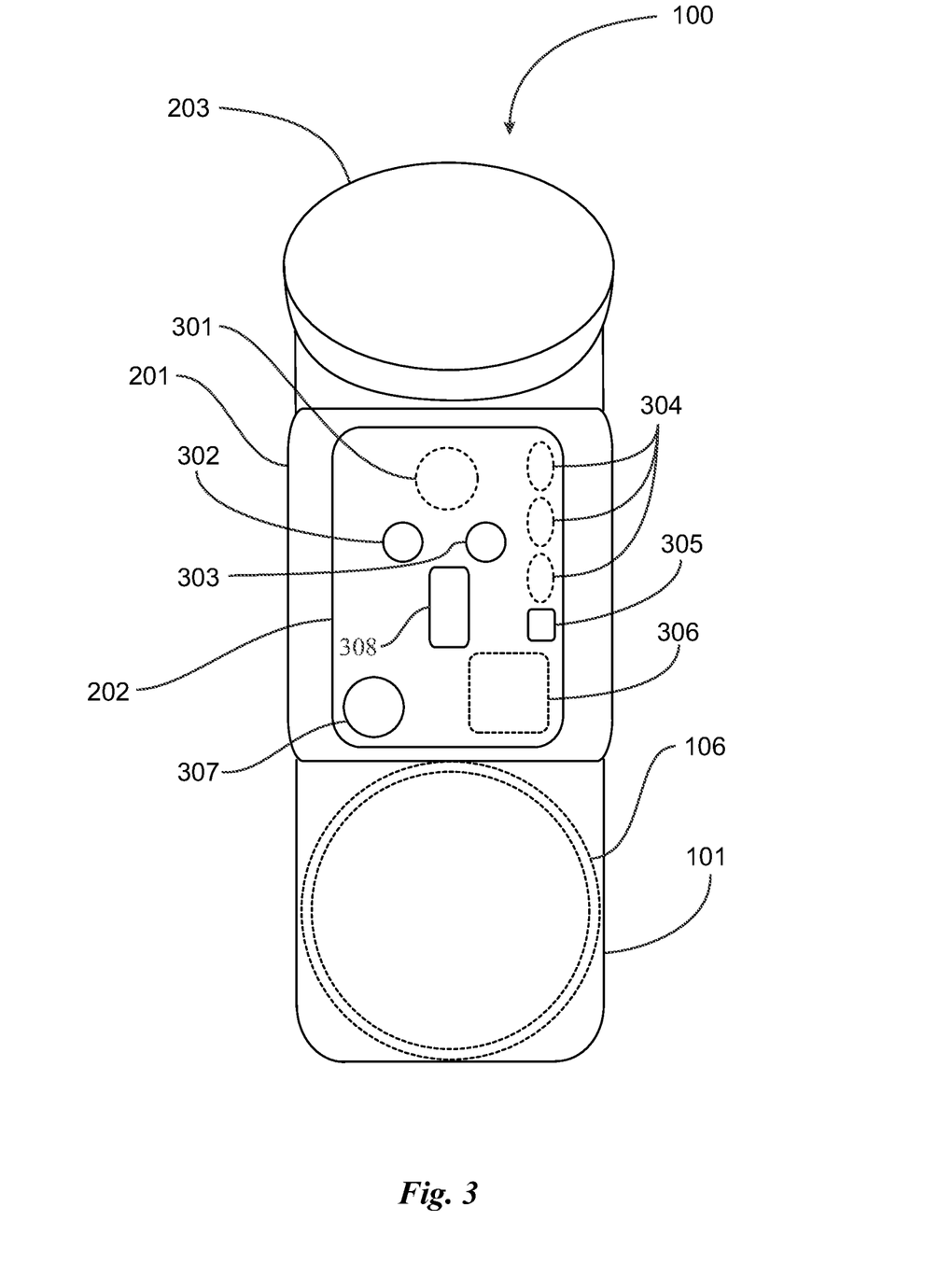
FIG. 3 is a rear elevation view of the MDI and electronic material sleeve of FIG. 2 depicting electronics according to an embodiment of the present invention.

FIG. 3 is a rear elevation view of MDI 100 supporting electronic material sleeve 201 of FIG. 2 depicting electronics according to an embodiment of the present invention. In this embodiment, some of the electronic components in electronic footprint 202 are encapsulated within the material of electronic sleeve 201 while other components are visible at the surface of the material. In this embodiment, all the electronic components are positioned away from patient opposite of mouthpiece cap 106.

Electronic footprint 202 includes a microprocessor 306 that supports computer aided processing including wireless local area network communication, or a version of Bluetooth™, and or radio frequency identification (RFID), or a similar wireless communications technology. Microprocessor 306 may be powered using one or more rechargeable batteries 304 having trace connections to other power consuming components. One known battery may be a Li ion or similar size rechargeable battery. Electronic footprint 202 includes any type of micro universal serial bus (USB) charging port 305 to enable device charging via a supporting computing device or USB charging adapter device. Any known type of electronic charging device may be implemented. Alternatively, disposable or rechargeable batteries may be implemented to power the electronic footprint 202.

In one embodiment, electronic footprint 202 includes an eccentric rotating motor (ERM) 301 to produce vibration upon receiving a signal from an electronic accessory device (not illustrated) detailed later in this specification. An audio speaker 307 is provided within electronics footprint 202 for producing a sound alert or notification sound upon receiving a signal from the fob device or, alternatively, in an automated operating mode, when electronics sleeve 201 is more than a preset distance, defined as out of wireless communications range, from the fob or other tracking implement such as a computing appliance, which in this embodiment, may be a smartphone.

In a preferred embodiment, the sound from speaker 307 is audible when the short range signaling and communication may become compromised because of a distance between devices, for example past 9-11, or more meters. In one embodiment, electronic footprint 202 includes at least one light emitting diode LED. In this embodiment there are two LEDs provided. One LED may be a strobe light or white light 302 while another LED may be a red light 303 arrayed adjacently and visible from outside of electronic sleeve 201. In this embodiment, only one light may be needed. In one embodiment, lights 302 and 303 may be adapted to flash alternately or in specific patterns to create a visual notification upon receiving a signal from the wirelessly paired fob device (FIG. 4A 400) or other tracking and communication device as previously disclosed. LEDs 302 and 303 may also provide state information relative to charging of electronic sleeve 201. Colors of LEDs may vary such as green and red, green and white, etc. LEDs may be actuated by receipt a wireless signal and or by an internal state notification command based on internal information or state.

Electronic sleeve 201 may be wirelessly connected to a computer, a cellular phone, and or a fob within range of the active wireless network used. In this embodiment, electronic sleeve 201 includes a patient help or call button 308. Button 308 may be operated by a patient in distress to communicate a signal or message to a network-based emergency service like 911, a medical response team service or a first responder medical service listening for such signals and or messages. In one embodiment, electronic sleeve 201 may include further electronic components that may be added to electronics footprint 202 such as a global positioning satellite (GPS) module, a wireless network modem, a subscriber identification module (SIM) or the like. In such an embodiment, electronics sleeve 201 may be located by an RF ID-based fob device or by another Bluetooth enabled device or appliance.

In one embodiment, electronic sleeve 201 may access a network server over a data network to provide a message alert to emergency medical personnel to summon medical help in an emergency like a severe asthma attack or an emergency canister refill requirement. A patient may locate MDI 100 supporting electronics sleeve 201 using a fob device or a Bluetooth enabled appliance as described above. A location signal sent by a fob device (RFID) or by a Bluetooth enabled device may cause ERM 301 to vibrate, and or LEDs 302 and or 303 to flash, and or speaker 307 to emit an audible sound thereby enabling a patient to quickly locate the MDI. In one embodiment, electronic sleeve 201 may be fabricated to custom fit a variety of inhaler body designs having variant geometric body forms, for example tubular forms, rectangular forms, or elliptical forms thereby allowing a patient to customize any stock hand-held inhaler device for wireless communication and tracking. Electronic sleeve 201 may be manufactured from stretchable transparent silicone capable of securely fitting a variety of aftermarket medical devices.

Figure 4A:
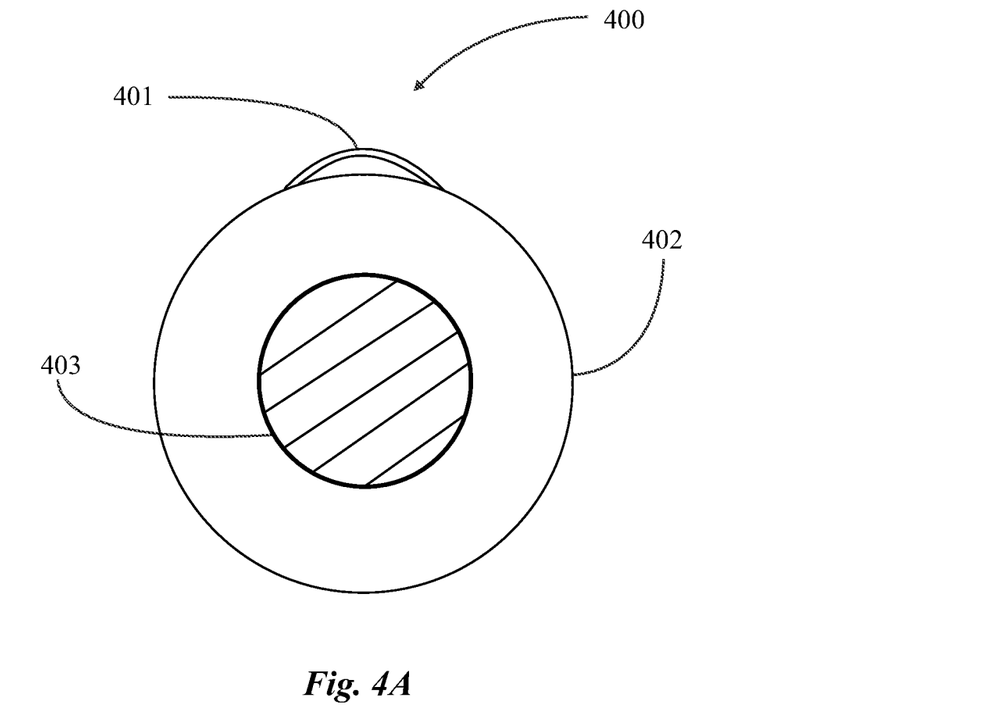
FIG. 4A is an overhead view of a fob device for wireless communication with the electronic material sleeve of FIG. 2.
Figure 4B:
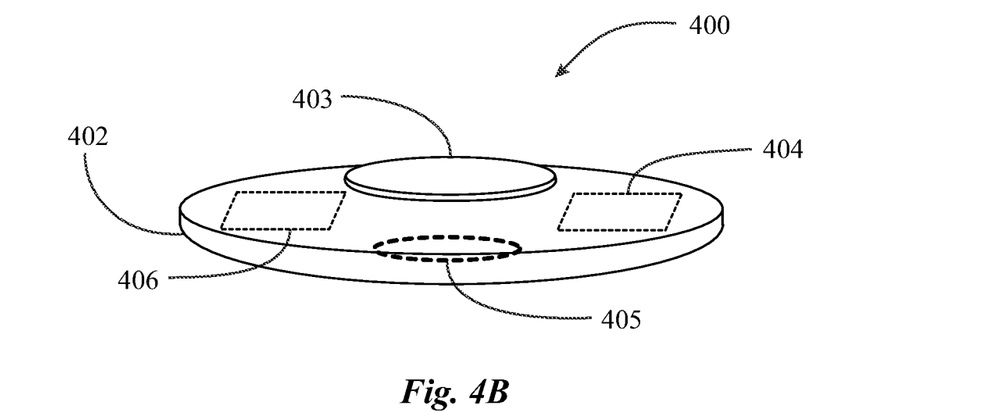
FIG. 4B is a perspective side view of the fob device of FIG. 4A.

FIG. 4A is an overhead view of a fob device 400 for tracking and communication with the electronic material sleeve of FIG. 3. FIG. 4B is a perspective side view of fob device 400 of FIG. 4A. Referring now to FIG. 4A, a fob device 400 is provided and depicted in an overhead view. fob 400 includes a wire loop 401 for enabling attachment of fob 400 to a lanyard, key ring, or other personal item always kept with the patient. fob device 400 includes a plastic body housing 402 with sufficient volume to house fob electronics components and power source (battery). fob device 400 includes a find button 403 that a user may depress to send a signal out to MDI 100 customized with electronic sleeve 201 (FIG. 3).

Referring to FIG. 4B, fob device 400 is depicted in a side view further illustrating a communications chip like RFID or a version of Bluetooth 404, and a battery 405 that may be snapped into or otherwise inserted into the bottom of fob device 400. In a preferred embodiment, fob device 400 is provided as a locator device and may employ RFID or any short range wireless communication such as a version of Bluetooth to locate electronic sleeve 201 (FIG. 3) if it is in range to receive the wireless signal. Fob device 400 may be adapted to work with an electronic sleeve that is exclusively identified to by code ID and may be marketed with the electronic sleeve for a specific brand of inhaler device. Additionally, a specific fob device may be paired with a specific electronic footprint 202 in a case where more than one individual in a given area or household operates paired fob/sleeve devices.

In another embodiment the fob device 400 may include additional electronic monitoring components in footprint 202 enabling monitoring of rate of respiration and or lung volume during respiration in order to detect a user in stress. Heart rate, blood pressure and other health conditions of a user may also be monitored. In this embodiment, if stress is identified by the fob device, the fob device may activate lights 302, motor 303, or sound emitter 301 to let the user know to keep the medical device near or to use the medical device. In one embodiment fob 400 may have a button 308 enabling alert of emergency medical services.

It is noted herein that electronic sleeve 201 may be provided for other types and brands of medical devices that are portable and required to prevent severe reaction in a patient such as an auto-injector which may inject epinephrine (Epi Pen™), for example.

Figure 5A:
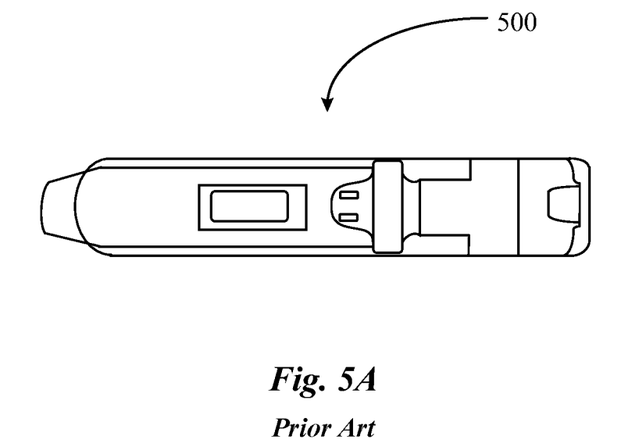
FIG. 5A is an elevation view of a fully assembled auto-injector pen according to current art.
Figure 5B:
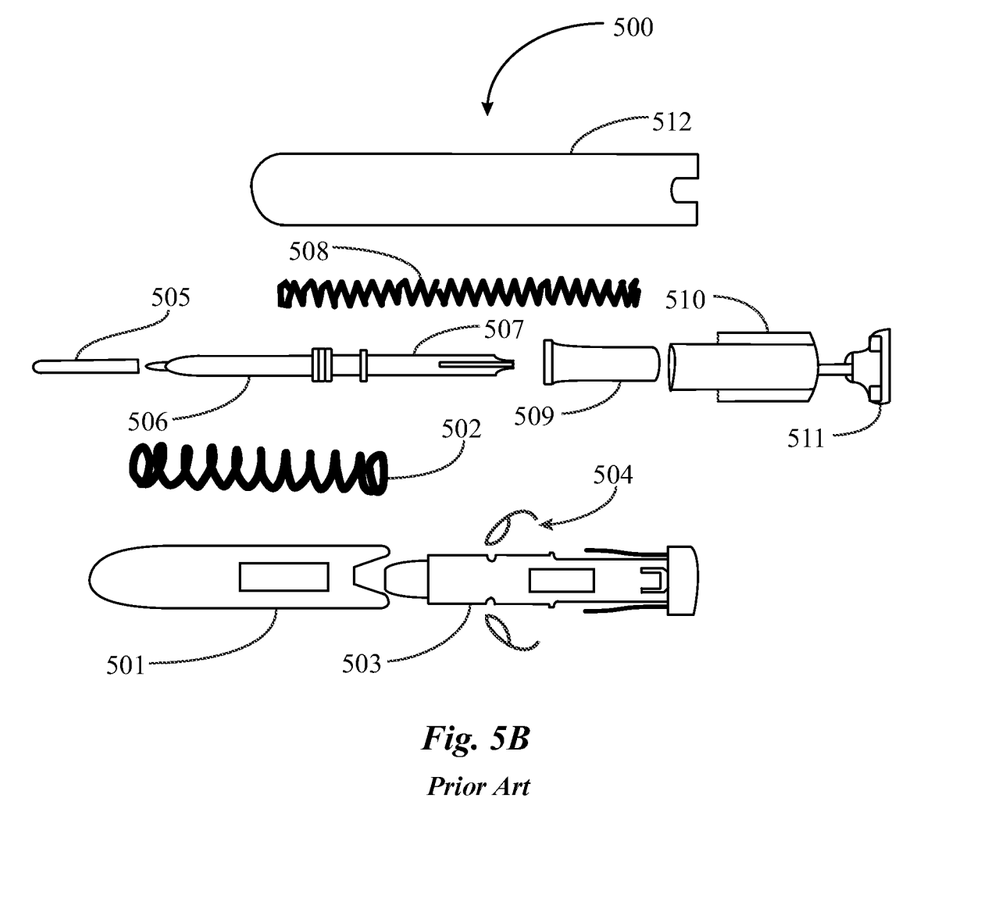
FIG. 5B is an exploded view of the auto-injector pen of FIG. 5A.

FIG. 5A is an elevation view of a fully assembled auto-injector 500 according to current art. FIG. 5B is an exploded view of auto-injector 500 of FIG. 5A. Referring now to FIG. 5A, auto-injector 500 is depicted in an assembled view. auto-injector is a brand of auto injector devices like device 500 that include other brand names as well. Typically, they all perform the same function of needle injection delivery of cartridge-based epinephrine, which is the primary medicine for countering an anaphylaxis shock event due to an allergic reaction in a patient with one or more serious allergies. Auto-Injector™ 500 is also typically a tubular device. Referring now to FIG. 5B, auto-injector 500 is depicted in a dissembled state for the purpose of revealing the atomic parts of the device. auto-injector 500 includes a housing 512 that protect and encloses all the other parts. auto-injector 500 induces a medicine cartridge 506 and a plunger 507. Cartridge 506 includes a needle for delivering a dose of epinephrine and a needle cover 505 covering the needle for safety purposes. Auto-injector 500 is driven by a drive spring 508 that is stopped at a release collar 509 that fits into a rear body 510. auto-injector 500 includes a carrier 503 and a shroud 501 that fit concentrically over parts 505, 506, 507, and 509. Carrier 503 includes a pair of control clips 504 that secure a control spring 502. It is noted herein that all the functional parts are assembled in concentric manner within tubular housing 512. A safety cap 511 is provided to cap off the rear of Auto-Injector™ 500. An actuator is internal and is activated when a patient or medical responder presses the needle side of Auto-Injector™ 500 against the skin to trigger a shot injection of a dose of the medication. Although this specification refers to Auto-Injector™ brand of auto-injector device, auto-injector devices of other brands may be substituted therefor.

Figure 6:
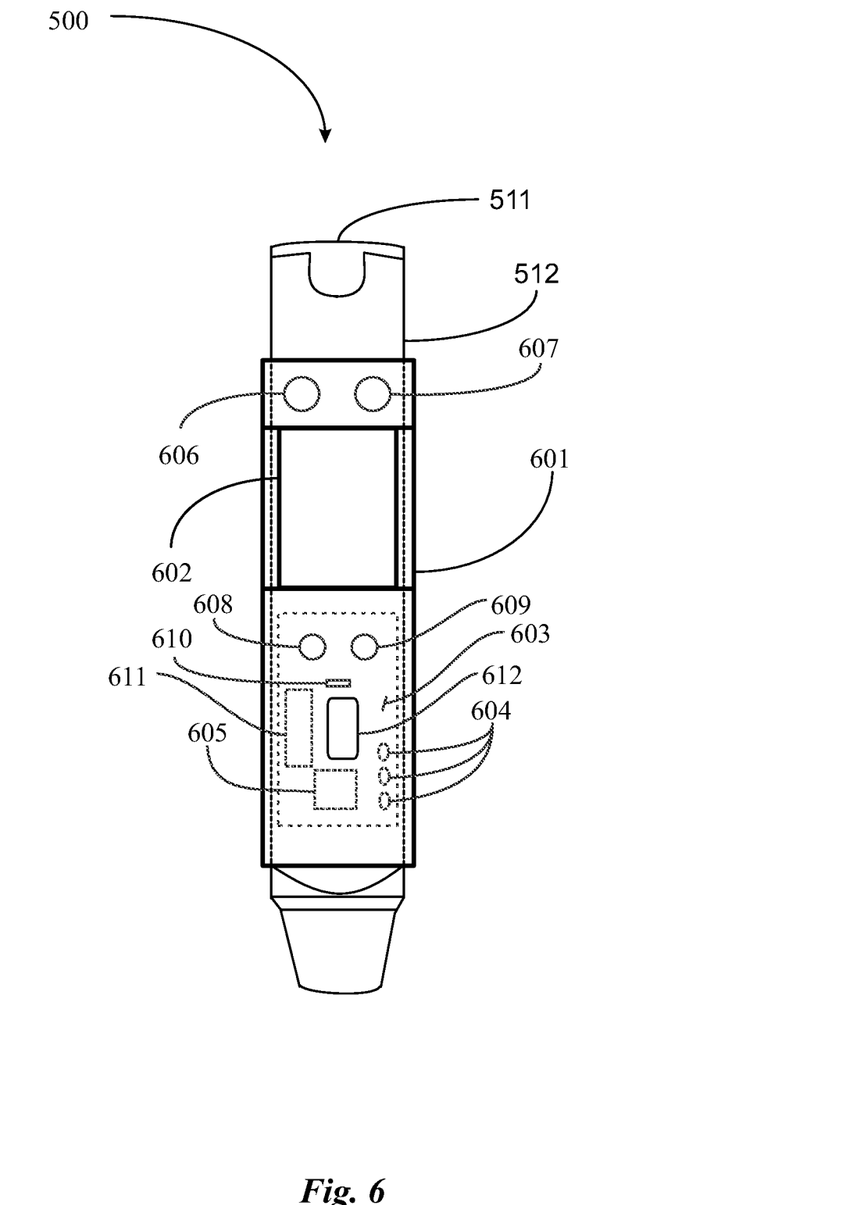
FIG. 6 is an overhead view of the Auto-Injector™ of FIG. 5A with an electronic material sleeve installed according to an embodiment of the present invention.

FIG. 6 is an overhead view of auto-injector 500 of FIG. 5A with an electronic material sleeve 601 installed thereon according to an embodiment of the present invention. auto-injector 500 is orientated vertically in this view with the needle side down and the cap side up. Auto-injector is modified in this embodiment with an electronic sleeve 601 that is adapted to be custom fitted over the rigid plastic tube housing 512 of auto-injector 500. Electronic sleeve 601 may be analogous in material composition to electronic sleeve 201 described further above. Electronic sleeve 601 may be molded in a tubular form from a medical grade elastic material like a silicone rubber composite. Electronics sleeve 601 is tubular in form in this embodiment and is flexible as well as resilient.

The inside diameter of electronic sleeve 601 is just smaller than the stock outside diameter of an auto-injector like auto-injector 500. In a preferred embodiment, the sleeve material is latex free, BPA free, water resistant, and of a medical grade material that can be sterilized. Electronic sleeve 601 may be stretched over and fitted onto the vertical tubular housing 512 of Auto-Injector™ 500 in a manner that is secure due to the elastic tension inherent to the sleeve. Other than silicone rubber, similar elastic materials like neoprene rubber or composites thereof may be substituted therefor. Electronic sleeve 601 has a wall thickness and an outside diameter wherein the wall thickness is sufficient to encapsulate electronic components and circuitry mostly confined to an electronics footprint 603 analogous to electronics footprint 202 described further above with reference to electronic sleeve 201 of FIG. 3A. In this view, electronic sleeve 601 has a transparent window 602 that may reside over the instructions typically printed on the outside of housing 512 of auto-injector 500.

In one embodiment, electronic sleeve 601 is fully transparent, in another embodiment, sleeve 601 is opaque except for transparent window 602. A user may operate auto-injector 500 without having to remove electronic sleeve 601. An auto-injector is designed to be used and then thrown away. Electronic skin 601 has a wall thickness that is large enough to host electronics in encapsulated state within the material or in partially encapsulated state where the component is visible and accessible from outside the sleeve. As such, some components are depicted in broken boundary (encapsulated) while some are visible (solid line).

In this embodiment, electronic footprint 603 contains at least one LED, in this body two, a red LED 608 and a white LED 609. One LED may be a white light while another LED may be a red light arrayed adjacently and visible from outside the electronic sleeve 601. In one embodiment, LED 608 and or LED 609 may be adapted to flash alternately, or in specific patterns to create a visual notification upon receiving a signal from a wirelessly paired or otherwise connected fob device and or providing information relative to charging state of electronic sleeve 601. Colors of LEDs 608 and 609 may vary such as green and red, green and white, etc. LEDs are actuated by a wireless signal and or by an internal state notification command. In this embodiment, LEDs 608 and 609 are arrayed above a charging port 610 and are disposed toward the needle end of electronic skin 601. Charging port 610 may be a micro-universal serial bus (USB) charge port to enable device charging via a USB supporting device via a USB cable.

Electronic sleeve 601 may include a microprocessor 605 that supports computer aided processing including wireless communication through a version of wireless local area network, for example Bluetooth LE™, and or radio frequency identification (RFID) or a similar wireless communications technology. Microprocessor 605 may be powered using one or more Li ion rechargeable batteries 604 having trace connections to other power consuming components. Microprocessor 605 may store and execute software and/or firmware enabling operation with the fob device, laptop or phone and communication outside of the wireless local area network, either via one of the connected computerized devices or autonomously via communication components within the footprint of the sleeve. Microprocessor 605 and Li ion batteries 604 may be disposed toward the needle end of auto-injector 500. In this view, transparent window 602 is disposed over the area of the auto-injector that includes the use instructions printed on the device. In one embodiment, transparent window 602 may extend all the way around the diameter of electronic sleeve 601.

In this embodiment, electronic skin 601 includes an eccentric rotating motor (ERM) 606 to produce vibration upon receiving a signal from an electronic fob accessory device detailed further below, and a sound emitter or audio speaker 607 to produce an amplified audio alert or notification sound upon receiving a signal from the fob device, or when it is detected that the sleeve and fob are separated by more than a specified distance, which may represent a boundary of effective communication within the wireless range. In a preferred embodiment, the sound from speaker 607 is audible past 10 or more meters. A help button 612 may be provided to electronic sleeve 601 that may be operated by a patient in distress to communicate a signal or message to a network-based emergency service like 911, a medical response team service or a first responder medical service listening for such signals and or messages. Electronic sleeve 601 may be wirelessly connected to a computer, a cellular phone, and a fob tracking device within range of an active wireless network.

In one embodiment, electronic sleeve 601 may include further electronic components that may be added to electronics footprint 602 such as a global positioning satellite (GPS) module, a wireless network modem, a subscriber identification module (SIM), or the like without departing from the scope of the invention. In such an embodiment, auto-injector 500 with sleeve 601 installed may be located by an RF ID based fob tracking device or by another Bluetooth enabled device or appliance. In one embodiment, electronic sleeve 601 may access a network server over a data network to provide an alert signal or message alert to emergency medical personnel or a medical response service to summon medical help in an emergency like a severe allergic reaction that requires immediate emergency personnel to be dispatched to the scene. In one embodiment, electronic material sleeve 601 may include an up-datable memory device 611 for storing data and firmware. Memory device 611 may be accessed by a patent for the purpose of offloading data, adding data, or synchronizing data using a computing appliance.

A location signal sent by a fob device (RFID) or by a Bluetooth™ enabled device may cause ERM 606 to vibrate, LEDs 608 and or white light or strobe light 609 to flash, and or speaker 607 to emit an audible sound thereby enabling a user to quickly locate auto-injector. Electronic sleeve 601 may be located using a phone or computing appliance running an application or a fob device like fob 404 described further above with respect to FIG. 4A and FIG. 4B. In one embodiment, electronic sleeve 601 may be fabricated to custom fit a variety of auto-injector body diameters thereby allowing a user to customize any auto-injector device for communication and tracking.

A patient may remove electronic sleeve 601 after an injection is achieved and place the sleeve over a second unused auto-injector that replaces the first one. In one embodiment, an auto-injector device may be reused (dependent upon capability) wherein a new cartridge may be inserted therein, and the mechanics of the device may be reset and or reactivated for subsequent use. In this body, a patient may keep electronic sleeve 601 on auto-injector 500 until the patient no longer desires to continue to reuse the same device.

Figure 7:
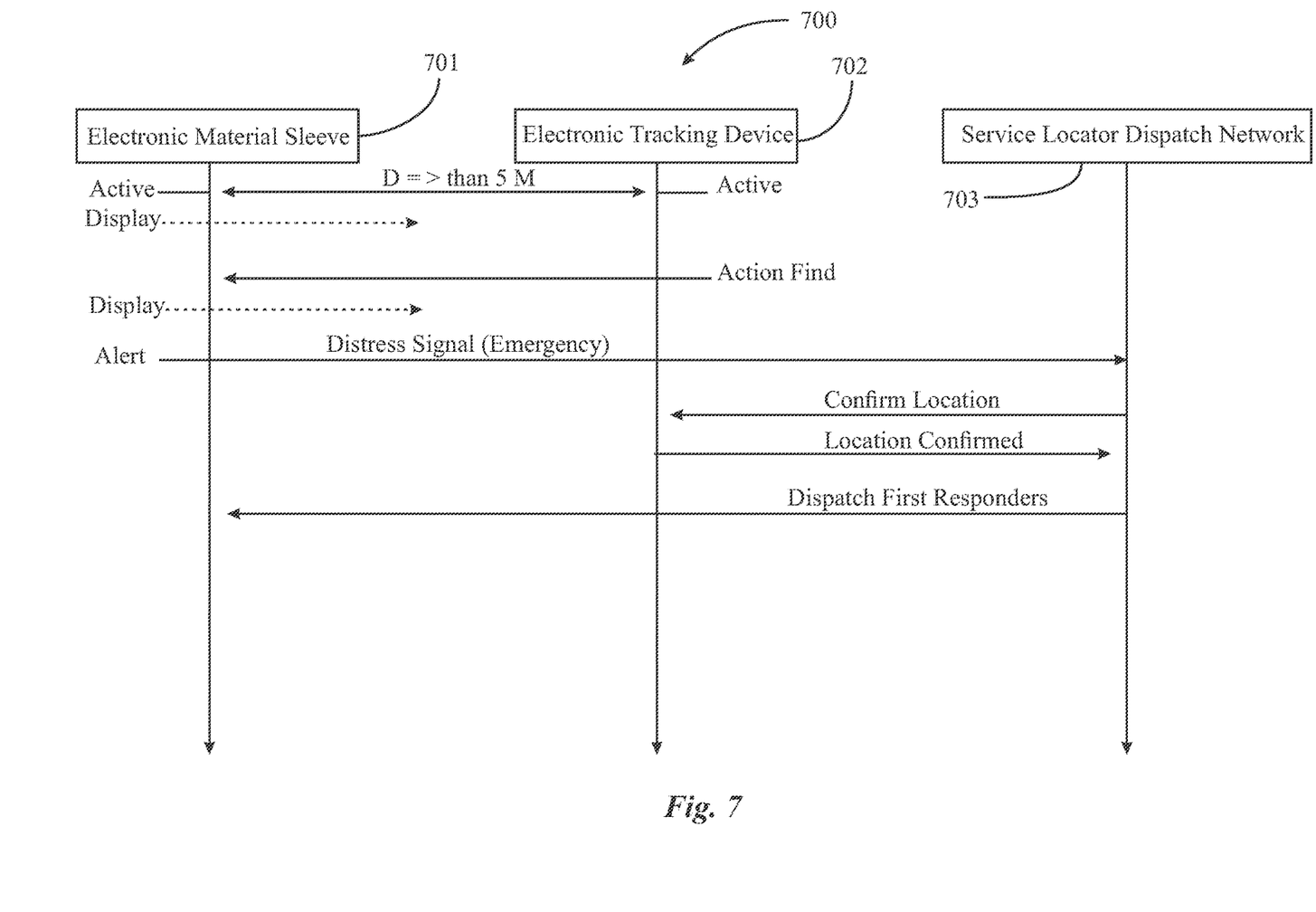
FIG. 7 is a sequence chart depicting sequences of interaction for locating an electronic material sleeve and for reporting an emergency alert requiring medical responders.

Referring now back to FIG. 4A and FIG. 4B, fob device 400 is adapted as a locator device, primarily, and may employ RFID or a version of Bluetooth™ to locate auto-injector 500 if it is in range to receive the wireless signal. Fob device 400 may be adapted to work with an electronic sleeve that it is exclusively identified to by code ID and may be marketed with the electronic sleeve for any specific brand of auto-injector device. In one embodiment, two electronic sleeves like sleeve 601 may be provided with a double pack of auto-injectors one sleeve already custom fitted to each device wherein a patient may first charge one electronic sleeve for one auto-injector to locate the pack when it is in range. It is noted herein that an auto-injector is good for about 18 months in terms of medicine expiration. Therefore, when batteries become low, electronic sleeve 601 may report that to a patient by a visual or wirelessly transmitted signal (dependent on capability) informing the patient of a need to recharge the electronic sleeve though the auto-injector has not yet been used. In this embodiment the same type of signaling by sleeve 601 may be used to indicate the medication may be expired FIG. 7 is a sequence chart 700 depicting sequences of interaction for locating an electronic material sleeve and for reporting an emergency alert requiring medical responders. Chart 700 represents an electronic material sleeve 701 which may be analogous to electronic sleeve 201 of FIG. 3A and to electronic sleeve 601 of FIG. 6. Electronic sleeve 701 is tracked using an electronic tracking device 702, which may be analogous to fob 400 of FIG. 4A, or which may be analogous to a patient's mobile cellular phone, or other Internet capable computing device. Chart 700 represents a network-based domain 703, which may be analogous to any cooperating emergency response location and dispatch service.

In a preferred embodiment, electronic tracking device 702 is in an active state and paired with or otherwise wirelessly connected to electronic material sleeve 701, which is also in a charged and active state. In one embodiment, an automated notification mode exists for a situation where a distance D between the electronic sleeve and tracking device becomes greater than a specified distance, which may represent a distance reflecting a boundary or near boundary of wireless service range. In auto mode, when the electronic sleeve 701 and the tracking device 702 are separated at near or beyond wireless range (whether Bluetooth, or RF-ID), an internal state notification signal may be executed locally on the electronic sleeve causing the electronic sleeve 701 to display flashing lights, vibration, and to sound an audio alert. A patient may be enabled to set distance for the devices short of losing wireless contact with electronic sleeve 701.

In another embodiment, a patient may execute an intended action by pressing a find button on a fob or by selecting a find option from a tracking software (SW) application executed and running on a tracking device where the tracking device is a cellular phone or a laptop computing device. Manually executing find may send a wireless signal (command) to electronic sleeve 701 to display in the same visual and audio manner as in auto mode by flashing lights, emitting audio, and vibrating. In one embodiment, a patient may program electronic sleeve 701 to only display light, only display sound, only display vibrating or to display a combination of those or all of those.

In one embodiment, electronic sleeve 701 includes a network modem and GPS location components required to access a wide area network (WAN) like the Internet network for example or a local emergency network. In one embodiment, electronic sleeve 701 includes a GPS/GPRS module, a user operable help button (network access), and an internal memory device or a secure digital (SD) memory card that fits into a card slot partially encapsulated within a wall of the electronic material sleeve 701, the memory device or card containing data about the patient including medical information, emergency service contact information, and contact information of family and friends. GPS/GPRS may enable a patient to locate electronic sleeve 701 (MDI sleeve, Auto-Injector™ sleeve) remotely using a network connected device like a cellular phone or laptop computer connected to the network. A user operable help button integrated into the electronic sleeve like help buttons 308 (MDI sleeve) or 612 (auto-injector sleeve) enable a patient in distress to send an alert by depressing the help button, the alert received by service locator dispatch point 703. Service 703 may offer a service that locates a response facility most local to the patient and may dispatch one or more individuals to the distress scene. Service 703 may use GPS/GPRS to locate that patient by locating the patient's tracking device (if GPS enabled) in the sleeve or alternatively, in the fob device. Once confirmed, responders may be dispatched to the location of the patient. In a variant of this embodiment, the service may locate the patient electronic sleeve (if GPS enabled). Tracking device 702 may use BT/RFID to locate electronic sleeve 701 if the sleeve is within range.

A patient or agent thereof may access memory on electronic sleeve 701 through a micro-USB port connection to a computing device in one embodiment. A patient may store and update patient data, or medicine availability data, or store other important data like medicine canister type and availability data, use state of the inhaler device (use counter), or other data deemed important to store in the electronic sleeve. Firmware (FW) updates may also be provided to update or replace FW on a microprocessor and other processing chip components of an electronic sleeve like sleeves 201 and 601 previously described. Tracking device 702 may be a fob device and may employ Bluetooth/RFID executed by depressing the fob button (find).

In one embodiment, tracking device 702 may be a fob device having RF and short-range wireless (Bluetooth™) transmitters wherein electronic sleeve 701 has the complimentary RF (tag) and short-range wireless (Bluetooth™) receivers provided within. In one embodiment, a patient or agent thereof may leverage USB capability on an electronic sleeve through a USB connection and using a SW application executed and running on a mobile device like a cellular phone or Laptop, and may configure the alert notification features of the electronic sleeve, selecting which features or combination of features sound, vibration, and or visible light, to activate and which if any to moot on the electronic sleeve.

Figure 8:
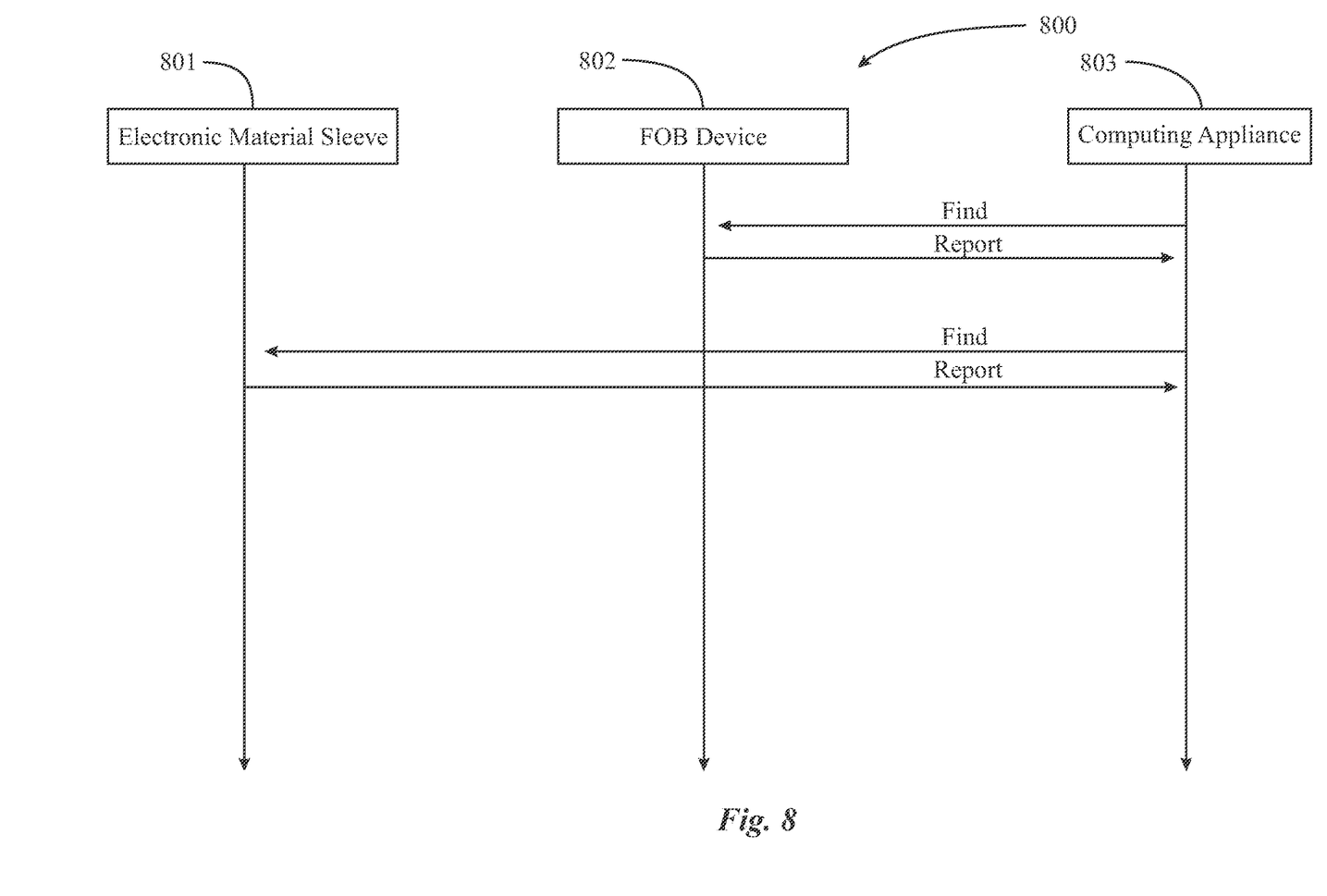
FIG. 8 is a sequence chart depicting sequences of interaction for finding an electronic material sleeve and for finding an associated fob device.

FIG. 8 is a sequence chart 800 depicting sequences of interaction for finding an electronic material sleeve and for finding an associated fob device using a computing appliance. Chart 800 represents interaction between an electronic material sleeve 801, a fob device 802, and a computing appliance 803. Computing appliance 803 may be a patient's mobile cellular phone, laptop computer, or other appliance capable of wireless communication. In this embodiment, both electronic sleeve 801 and fob 802 are Bluetooth™ capable and can communicate with computing appliance 803. In one embodiment, commuting appliance includes a small software (SW) application that provides a user interface having selective options for connecting wirelessly to each device and options for pinging or signaling those devices to at least display sound, light, and vibration sufficient to reveal location in a local sense.

For example, a patient may use computing appliance 803 to find fob device 802 by selecting "Find fob" in an application user interface (UI) executed from memory on the computing appliance. fob 802 may respond to a request sent by sounding, flashing, and vibrating such that a patient operating the computing appliance may notice the location by seeing, hearing, and feeling. Similarly, a patient may use computing appliance 803 to find or locate electronic sleeve 801 in the same fashion. Electronic sleeve 801 may, in one embodiment, be adapted under programed conditions to access a network access point on a network through a network modem and report the current GPS location thereof for emergency response purposes or simply so it may be found by a patient who may have left it or lost it somewhere between uses. Programming electronic sleeve 801 may include loading data onto a memory provided within the sleeve and available to the microprocessor including contact information for family, friends, doctors, or emergency dispatch services.

The electronic material sleeve 801, through both passive and active alert systems (RFID and Bluetooth™), may greatly improve the chance that the medication required by a patient will be immediately available to the patient whenever and wherever needed. The inhaler skin alert/find processes use the fob (token, charm, pendant, etc.) which can easily be carried everyday on a user's body via bracelet, necklace or other wearable device. Alternatively, the device may be attached or integrated with a user's phone, keys, or wallet.

In one embodiment, the user may activate the fob device or other computerized device like a phone or laptop to signal a find function for the emergency medication dispensing device, wherein anyone or more of the LEDs, sound emitters, and ERM of an associated electronic sleeve may activate. The microprocessor software/firmware in the sleeve footprint 603 may monitor for medication usage after activation of the sleeve, via anyone of a motion sensor or sensing if medication has been dispensed. If the microprocessor fails to detect usage of the medication in the device, or the user does not deactivate the sleeve device alerts, via the fob or other computerized device an emergency message may be sent to an emergency medical facility to make contact with the user and/or send emergency medical professionals, for example via ambulance or fire department to a premises where the user may be located.

It will be apparent to one with skill in the art that the electronic material sleeve of the present invention may be provided using some or all the elements described herein. The arrangement of elements and functionality thereof relative to the electronic material sleeve of the invention is described in different embodiments each of which is an implementation of the present invention. While the uses and methods are described in enabling detail herein, it is to be noted that many alterations could be made in the details of the construction and the arrangement of the elements of the electronic material sleeve without departing from the spirit and scope of this invention. The present invention is limited only by the breadth of the claims below.

The invention claimed is:

1. An electronic sleeve adapted to fit over an emergency medication dispensing device comprising:
    an elastic cylindrical electronic sleeve formed by a tubular wall of flexible material having a diameter and a length greater than the diameter, the sleeve having a top unobstructed open end and a bottom unobstructed open end;
    a microprocessor and associated circuitry encapsulated entirely within a thickness of the wall of the electronic sleeve, the circuitry including at least wireless communications capability;
    at least one battery encapsulated within the thickness of the wall providing power to the microprocessor and the circuitry;
    at least one LED at least partially encapsulated within the wall of the electronic sleeve and visible from outside of the wall; and
    at least one sound emitter at least partially encapsulated within a wall of the electronic sleeve;
    characterized in that the electronic sleeve is not involved in an operation process of the emergency medication dispensing device and activates any one or more of the LED and sound emitter in response to a command signal.

2. The electronic sleeve of claim 1, wherein at least one eccentric rotating motor (ERM) is included and adapted to vibrate encapsulated within the wall of the electronic sleeve.

3. The electronic sleeve of claim 2 wherein, upon receipt of a wireless command from an electronic fob device, the electronic sleeve emits a signal comprised of at least one of the at least one LED flashing for visual reference, the at least one speaker emitting sound for audio reference, and the electronic motor vibrates for tactile reference.

4. The electronic sleeve of claim 2 wherein, upon detection of breech of an amount of distance established as a maximum boundary between the electronic sleeve and another electronic device having a wireless connection to the electronic sleeve, the electronic sleeve emits a signal comprised of at least one of the at least one LED flashing for visual reference, the at least one speaker emitting sound for audio reference, and the electronic motor vibrating for tactile reference.

5. The electronic sleeve of claim 4, wherein the breech of distance is detected locally on the electronic sleeve.

6. The electronic sleeve of claim 1, further including a transparent window enabling visual access to instructions printed on the emergency medication dispensing device.

7. The electronic sleeve of claim 1, wherein the command signal is received from a fob device using a short-range wireless communication technology.

8. The electronic sleeve of claim 7, wherein the command signal is received from a mobile computing appliance using any one of radio frequency identification (RFID) and a version of Bluetooth™ wireless technology.

9. The electronic sleeve of claim 8, wherein the mobile computing appliance is a cellular phone.

10. The electronic sleeve of claim 1, further including a network modem and global positioning satellite (GPS) module.

11. The electronic sleeve of claim 1, wherein the wall thickness is larger on one side of the sleeve and wherein the larger thickness area is host to the encapsulated and partially encapsulated electronics.

12. The electronic sleeve of claim 1, further including a memory device encapsulated within a wall of the electronic sleeve, the memory device containing data about the patient including medical information, emergency service contact information, and contact information of family and friends.

13. The electronic sleeve of claim 1, wherein a charge port is included and also functions as a data port for transfer of data to or from the electronic material sleeve.

14. The electronic sleeve of claim 1, wherein one of the one or more tasks performed is recording medication use events to determine reportable statistics including usage frequency, dose amount, and medication amount remaining in a loaded cartridge.

15. A method of locating an emergency medication dispensing device comprising the steps of:
    placing an electronic sleeve around the emergency medication dispensing device, the electronic sleeve comprising an elastic cylinder formed by a tubular wall of flexible material having an open, unobstructed top end and an open unobstructed bottom end, and having a diameter and a length, the length greater than the diameter, and electronic components embedded entirely within a thickness of the tubular wall including at least circuitry providing wireless communication including at least a microprocessor storing and executing software, the electronic components including at least one LED and a sound emitter, and the electronic sleeve is not involved in an operation process of the emergency medication dispensing device;

wirelessly connecting an electronic mini fob device to the microprocessor;

manipulating the mini fob device to activate the at least one LED and sound emitter enabling a user to find and use medication in the emergency medication dispensing device.

16. The method of claim 15, wherein at least one eccentric rotating motor (ERM) is included and adapted to vibrate encapsulated within the wall of the elastic cylinder.

17. The method of claim 16 wherein, upon receipt of a wireless command from an electronic fob device, the electronic sleeve emits a signal comprised of at least one of the at least one LED flashing for visual reference, the at least one speaker emitting sound for audio reference, and the electronic motor vibrating for tactile reference.

18. The method of claim 16 wherein, upon detection of breech of an amount of distance established as a maximum boundary between the electronic sleeve and another electronic device having a wireless connection to the electronic sleeve, the electronic sleeve emits a signal comprised of at least one of the at least one LED flashing for visual reference, the at least one speaker emitting sound for audio reference, and the electronic motor vibrating for tactile reference.

* * * * *